US008021342B2

(12) United States Patent
Girgis et al.

(10) Patent No.: US 8,021,342 B2
(45) Date of Patent: Sep. 20, 2011

(54) LIQUID MEDICATION DISPENSER

(76) Inventors: Deborah Girgis, Glendale, CA (US); Victoria Lombardi, Glendale, CA (US)

( * ) Notice: Subject to any disclaimer, the term of this patent is extended or adjusted under 35 U.S.C. 154(b) by 1186 days.

(21) Appl. No.: 11/592,401

(22) Filed: Nov. 3, 2006

(65) Prior Publication Data

US 2008/0105707 A1 May 8, 2008

(51) Int. Cl.
*A61M 5/00* (2006.01)

(52) U.S. Cl. ........ 604/187; 604/218; 604/246; 604/248; 604/257; 604/258; 604/221; 604/211; 604/135; 604/203; 604/226; 604/181; 604/191; 222/144; 222/144.5; 222/145.1; 222/129; 222/145.5

(58) Field of Classification Search .................... 604/86, 604/183–184, 187, 135, 211, 221, 231, 238, 604/222, 181, 207–208, 218, 246, 248, 257–259; 222/144, 145.1, 144.5
See application file for complete search history.

(56) References Cited

U.S. PATENT DOCUMENTS

| | | | | |
|---|---|---|---|---|
| 212,046 | A * | 2/1879 | Palmer | 604/183 |
| 551,424 | A | 12/1895 | Wheeler | |
| 984,037 | A * | 2/1911 | Sheets | 604/125 |
| 2,613,537 | A | 10/1952 | Addario | |
| 3,128,920 | A | 4/1964 | Volckening et al. | |
| 4,702,737 | A | 10/1987 | Pizzino | |
| 5,007,743 | A | 4/1991 | Brennan | |
| 5,645,534 | A * | 7/1997 | Chanoch | 604/189 |
| 5,646,912 | A | 7/1997 | Cousin | |
| 6,126,642 | A | 10/2000 | Kriesel et al. | |
| 6,558,358 | B2 | 5/2003 | Rosoff et al. | |
| 6,860,390 | B2 | 3/2005 | Bowman | |
| 2004/0024372 | A1 | 2/2004 | Grogan | |
| 2004/0182873 | A1 | 9/2004 | Baum | |
| 2004/0251165 | A1 | 12/2004 | Girzaitis | |
| 2004/0267201 | A1 * | 12/2004 | Agerup | 604/152 |

* cited by examiner

*Primary Examiner* — Theodore Stigell
*Assistant Examiner* — Edelmira Bosques
(74) *Attorney, Agent, or Firm* — Weiss & Moy, P.C.; Aaron C. Fong

(57) ABSTRACT

A liquid medication dispenser includes a housing that has open top and bottom. The housing includes a central channel and a plurality of internal compartments disposed around the central channel. Each internal compartment is configured to hold liquid medication. The central channel is provided with symmetrically disposed bottom apertures configured to open into respective internal compartments. A shaft is configured to rotate and advance within the central channel. The shaft has a bottom hollow portion and at least one lateral aperture thereon configured to align with each one of the bottom channel apertures. The lateral shaft aperture aligns with a respective bottom channel aperture to allow transfer of liquid medication under gravity from the corresponding internal compartment into the bottom hollow portion of the shaft. The bottom hollow portion is apertured at one end to allow for transferred liquid medication to drip out of the dispenser in a controlled fashion.

35 Claims, 6 Drawing Sheets

LIQUID MEDICATION DISPENSER

COPYRIGHT NOTICE

Portions of the disclosure of this patent document may contain material that is subject to copyright and/or mask work protection. The copyright and/or mask work owner has no objection to the facsimile reproduction by anyone of the patent document or the patent disclosure, as it appears in the U.S. Patent and Trademark Office patent file or records, but otherwise reserves all copyright and/or mask work rights whatsoever.

BACKGROUND

Medication recipients frequently need to take a set dose of liquid medication at regular intervals of time. Failure to take the required medication dosage at required time intervals interferes with the prescribed treatment regimen. Liquid medication dosages are typically measured by pouring the medication into a small container via a medicine dropper prior to taking the medication. This manner of on-the-spot dosage measurement is inconvenient and prone to error. Patients who take numerous medications on a regular basis can easily loose track of the time of day or night at which a particular medication was most recently taken. The end result may be an omission by the patient to take the required dosage or exceeding the dosage requirement.

The same problems are being faced by parents or caregivers of children of young age. Frequently, oral antibiotic has to be carried around all day as parents or caregivers go through their daily routine with the child. Since liquid medications must often be given at different times of the day, it would be desirable to have a portable liquid medication dispenser which allows an individual to easily organize and administer one to four dosages per day, as needed.

SUMMARY

Some embodiments disclosed herein are generally directed to a liquid medication dispenser.

In accordance with one aspect of the present invention, the liquid medication dispenser comprises a housing with an open top. The housing includes a central channel and at least one internal compartment disposed around the central channel. The internal compartments are configured to hold liquid medication. The central channel includes at least one bottom aperture configured to open into a respective internal compartment. The dispenser also includes a shaft configured to rotate and advance within the central channel.

The shaft includes an elongated bottom hollow portion with a lateral aperture thereon. The elongated bottom hollow portion is configured to receive liquid medication via the lateral aperture. The lateral shaft aperture is configured to align with a respective bottom channel aperture when the shaft is advanced a pre-set distance and rotated a pre-set amount within the central channel. The alignment permits transfer of liquid medication under gravity from the respective internal compartment into the elongated bottom hollow portion. The elongated bottom hollow portion is apertured at one end to allow transferred liquid medication to drip out in a controlled fashion.

In accordance with another aspect of the present invention, the liquid medication dispenser comprises a housing with an open top. The housing includes a central channel and at least one internal compartment disposed around the central channel. Each internal compartment is configured to hold liquid medication. The dispenser also comprises a top ring configured to close off the open top of the housing. The top ring has a central opening. A dispenser cap is disposed over the top ring. At least one spring is operatively coupled between the dispenser cap and the top ring. The spring is naturally biased away from the top ring. The central channel includes at least one bottom aperture configured to open into a respective internal compartment. The dispenser also includes a shaft secured at one end to the underside of the dispenser cap via the central opening of the top ring and the spring. The shaft is configured to rotate and advance within the central channel.

The shaft includes an elongated bottom hollow portion with a lateral aperture thereon. The elongated bottom hollow portion is configured to receive liquid medication via the lateral aperture. The lateral shaft aperture is configured to align with a respective bottom channel aperture when the shaft is advanced a pre-set distance and rotated a pre-set amount within the central channel. The alignment permits transfer of liquid medication under gravity from a respective internal compartment into the elongated bottom hollow portion which is apertured at one end to allow transferred liquid medication to drip out in a controlled fashion.

In accordance with yet another aspect of the present invention, the liquid medication dispenser comprises a housing including an open top, an open dispenser tip disposed away from the open top, a central channel connecting the open top and the open dispenser tip, and at least one internal compartment disposed around the central channel. Each internal compartment is configured to hold liquid medication. The housing has an outer wall provided with a plurality of markings. Each of the markings signifies selection of a respective internal compartment.

A top ring is configured to close off the open top of the housing. The top ring has a central opening. A dispenser cap is disposed over the top ring. The top surface of the dispenser cap is marked in at least one location. A spring assembly is operatively coupled between the dispenser cap and the top ring. The spring assembly is naturally biased away from the top ring. The central channel is provided with one or more bottom apertures with each aperture configured to open into a respective internal compartment.

A shaft is secured at one end to the underside of the dispenser cap via the central opening of the top ring and the spring assembly. The shaft is configured to rotate and advance within the central channel. The shaft includes an elongated bottom hollow portion with a lateral aperture thereon. The elongated bottom hollow portion is configured to receive liquid medication via the lateral aperture. The lateral shaft aperture is configured to align with one of the bottom channel apertures when the shaft is advanced a pre-set distance and rotated a pre-set amount within the central channel.

This alignment permits transfer of liquid medication under gravity from the respective internal compartment into the elongated bottom hollow portion. The elongated bottom hollow portion is apertured over the open dispenser tip to allow transferred liquid medication to drip out of the open dispenser tip in a controlled fashion. The rate of liquid medication drip out of the open dispenser tip is controlled by varying the orientation of the dispenser tip relative to a horizontal surface.

These and other aspects of the invention will become apparent from a review of the accompanying drawings and the following detailed description of the invention.

BRIEF DESCRIPTION OF THE DRAWINGS

The present invention is generally shown by way of reference to the accompanying drawings in which.

DETAILED DESCRIPTION

The detailed description set forth below in connection with the appended drawings is intended as a description of illustrated exemplary embodiments and is not intended to represent the only forms in which these embodiments may be constructed and/or utilized. The description sets forth the functions and sequence of steps for constructing and operating the present invention in connection with the illustrated embodiments. However, it is to be understood that the same or equivalent functions and/or sequences may be accomplished by different embodiments that are also intended to be encompassed within the spirit and scope of the present invention.

Some embodiments of the present invention will be described in detail with reference to a liquid medication dispenser, as generally shown in FIGS. 1-7. Additional embodiments, features and/or advantages of the invention will become apparent from the ensuing description or may be learned by practicing the invention. In the attached figures, the various drawings are not to scale with like numerals referring to like features throughout both the drawings and the description.

Figure 1:
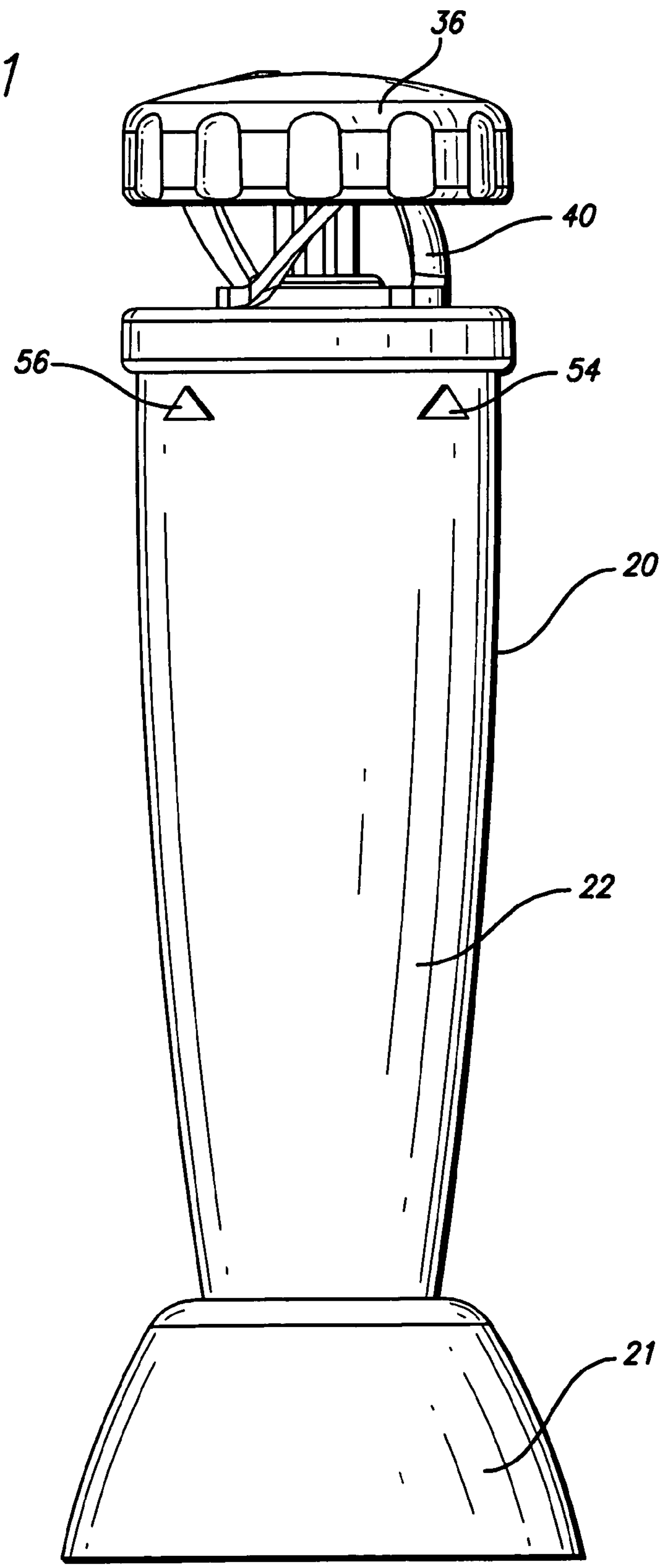
FIG. 1 is a front perspective view of a liquid medication dispenser coupled to a stand in accordance with the present invention.
Figure 2:
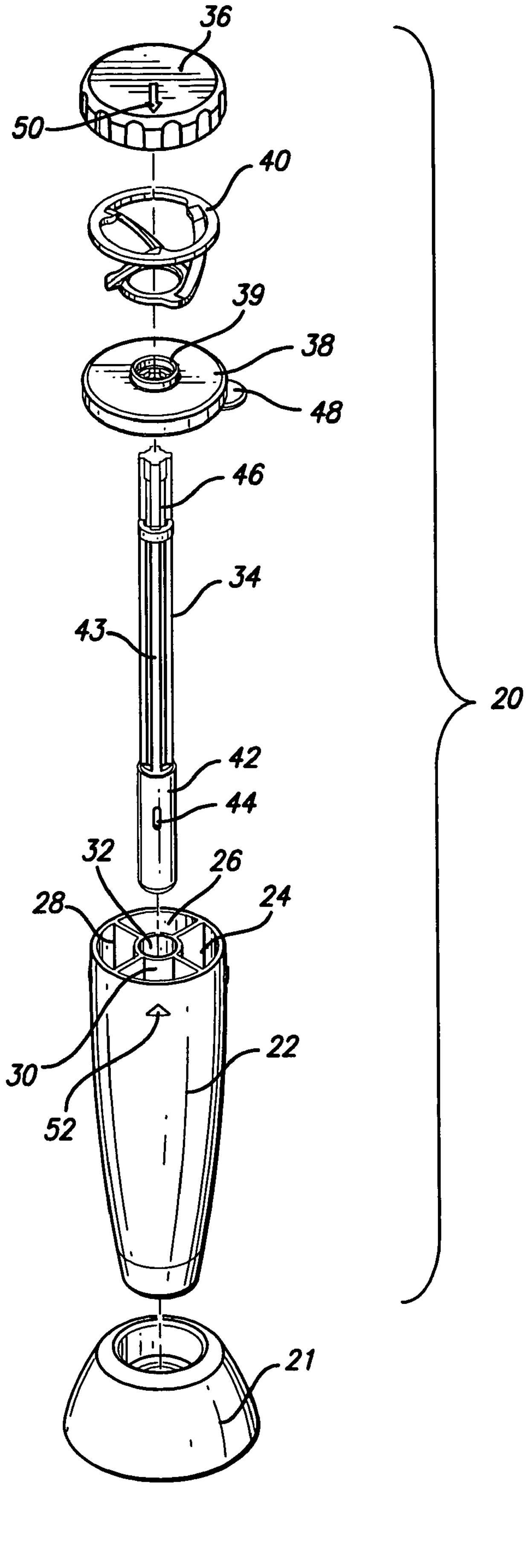
FIG. 2 is an exploded perspective view of the liquid medication dispenser and stand of FIG. 1.
Figure 6:
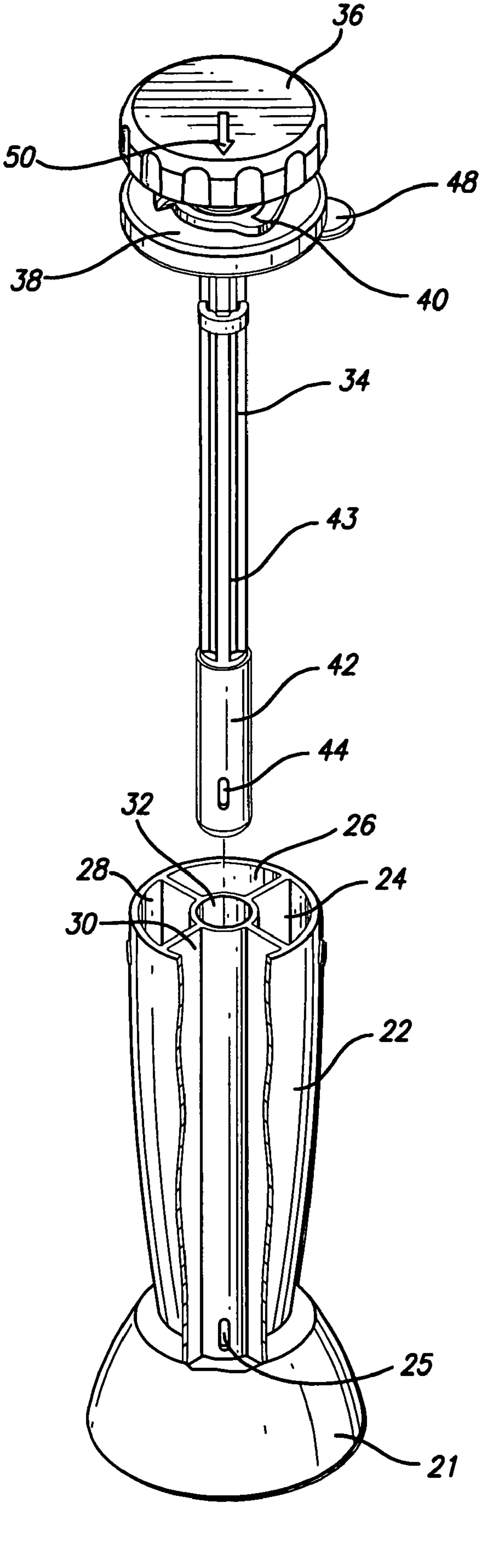
FIG. 6 is a partially cut away perspective view of the liquid medication dispenser and stand of FIG. 1.

FIG. 1 is a front perspective view of a portable liquid medication dispenser 20 in accordance with an exemplary embodiment of the present invention. Liquid medication dispenser 20 may be removably coupled to a portable stand 21 when not in use. Liquid medication dispenser 20 includes a housing 22 which, generally, has an inverted frusto-conical shape (FIGS. 1-2). Housing 22 is provided internally with four compartments 24, 26, 28 and 30 (FIG. 2) which are symmetrically disposed around a central channel 32 (FIG. 2). Each compartment (24, 26, 28 and 30) is configured to store a pre-set quantity of liquid medication. Central channel 32 is configured to accommodate a shaft 34 (FIG. 2) which is adapted to rotate within channel 32. Central channel 32 is provided with four bottom apertures with each aperture opening into a respective compartment. For example, bottom aperture 25 opens into compartment 30, as generally depicted in FIG. 6.

Shaft 34 slides in/out of channel 32 for maintenance or during assembly/disassembly, as needed. One end of shaft 34 is secured to the underside of a dispenser cap 36 via a top ring 38 and associated spring 40 (FIG. 2). Shaft 34 includes a generally elongated hollow bottom portion 42 which is provided with a lateral aperture 44 (FIG. 2). Lateral aperture 44 is configured to align with each one of the four bottom apertures (e.g., bottom aperture 25) on central channel 32 as shaft 34 is pushed in and rotated within central channel 32 by the user during operation of the device. Shaft 34 also includes a solid ribbed top portion 46 (FIG. 7) which is frictionally fitted through central opening 39 of top ring 38 and secured to the underside of cap 36 (FIG. 7) during device assembly. Shaft 34 further includes a ribbed intermediate portion 43 (FIGS. 2, 6-7) which is coupled between top and bottom portions 46 and 42, respectively. Shaft 34 may be molded as one piece or assembled from portions 42, 43 and 46, as desired.

Figure 3:
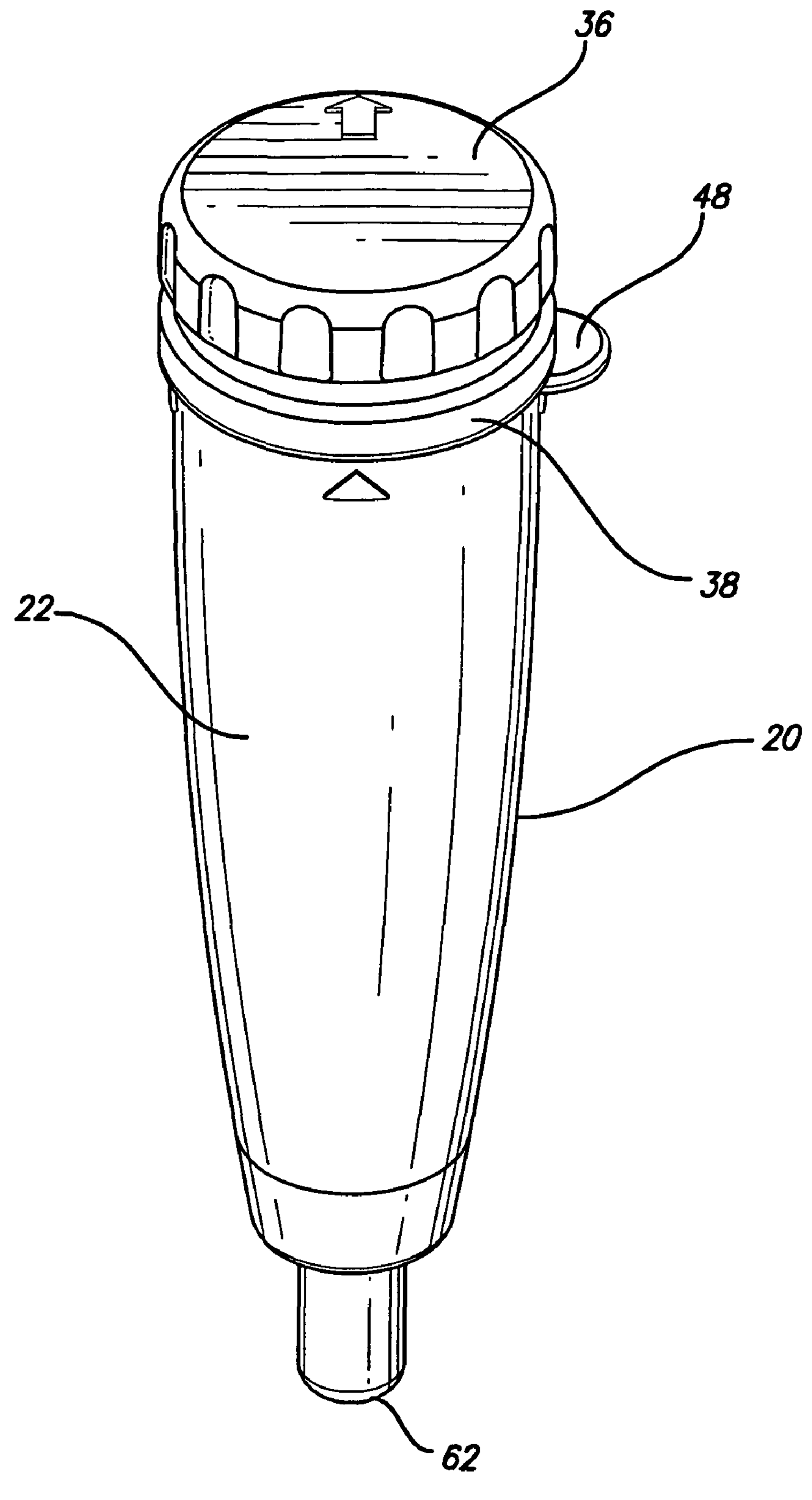
FIG. 3 is a side perspective view of the liquid medication dispenser of FIG. 1.
Figure 7:
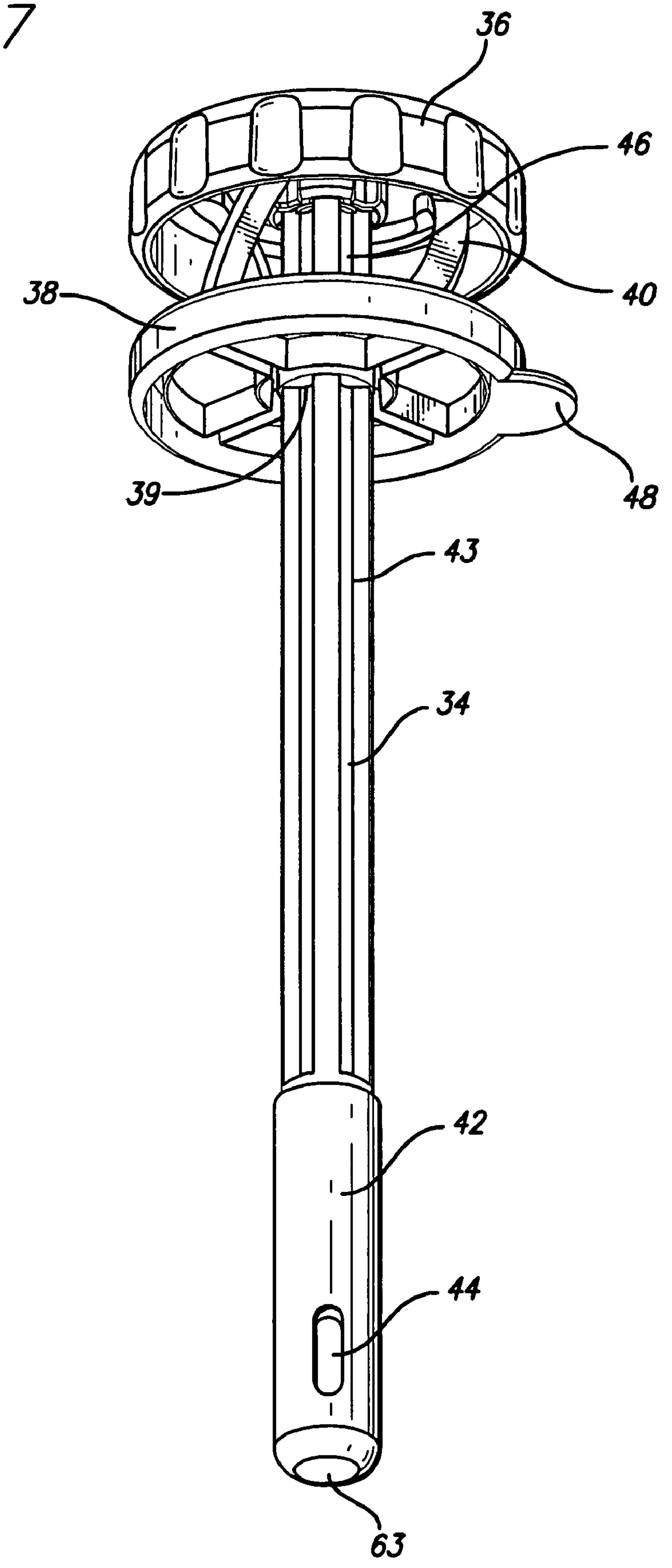
FIG. 7 is a bottom perspective view of various components of the liquid medication dispenser of FIG. 1.

Spring 40 is operatively coupled between top ring 38 and the underside of dispenser cap 36, as generally illustrated in reference to FIG. 7. Spring 40 is naturally biased upwards, i.e. away from top ring 38 (FIG. 7). Top ring 38 is configured to snap over the open top of housing 22 after each compartment has been filled with liquid medication (FIG. 3). Top ring 38 serves as a housing cap preventing the filled compartments from spilling liquid medication during handling or storage. Top ring 38 includes a side tab 48 which may be gripped by the user during removal of top ring 38 from housing 22.

Figure 4:
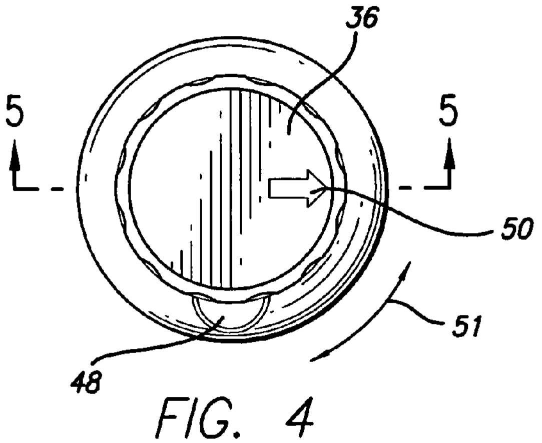
FIG. 4 is a top view of the liquid medication dispenser of FIG. 3 with the dispenser cap rotated 90° in a clockwise direction.

When properly assembled, rotation of dispenser cap 36 clockwise or anti-clockwise, as generally depicted at 51 in FIG. 4, would result in corresponding rotation of shaft 34 within central channel 32. As generally shown in reference to FIG. 2, spring 40 is appropriately configured to allow rotation of cap 36 relative to top ring 38 which is fixed over (secured to) housing 22. Spring 40 may be made of resilient, durable plastic and/or any other suitable material(s).

During device operation, the user would rotate cap 36, as generally depicted at 51 in FIG. 4, until arrow 50 (FIG. 2), which may be etched or otherwise marked on the top surface of dispenser cap 36, aligns with one of four corresponding markings on the outer wall of housing 22. For example, FIG. 2 shows arrow 50 being generally aligned with marking 52 on the outer wall of housing 22. Marking 52 signifies selection of internal compartment 30 (FIG. 2). FIG. 1 generally depicts markings (indicia) 54, 56 which correspond to other internal compartments, respectively.

Figure 5A:
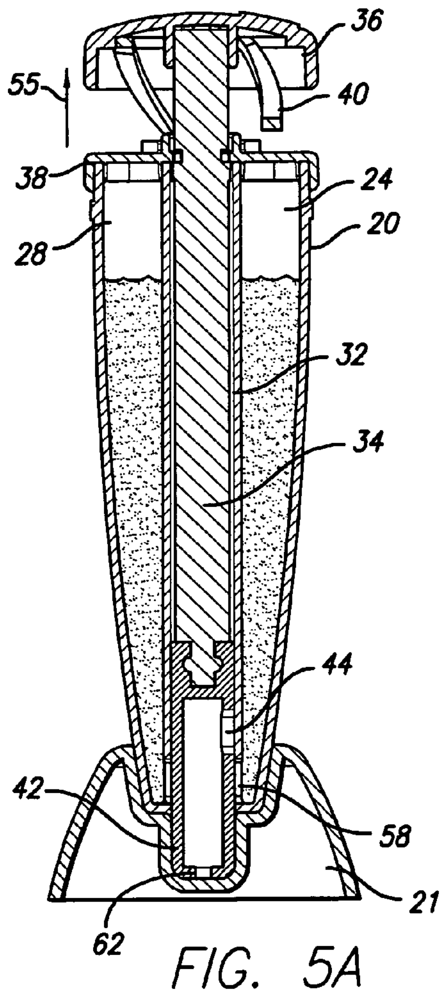
FIG. 5A is a cross-sectional view along section line 5-5 of FIG. 4 with the dispenser cap in an uncompressed state.
Figure 5B:
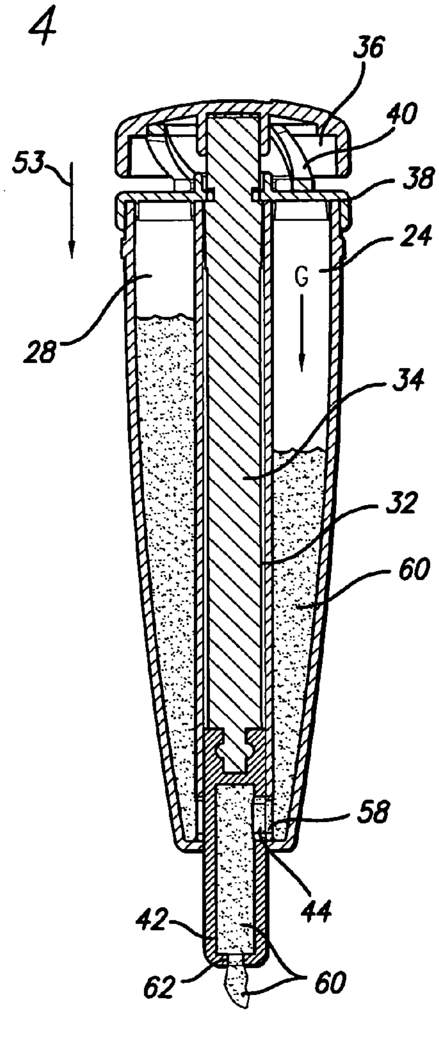
FIG. 5B is a cross-sectional view along section line 5-5 of FIG. 4 with the dispenser cap in a compressed state.

When arrow 50 is properly aligned with one of the four markings (indicia) on the outer wall of housing 22, the user compresses dispenser cap 36 toward top ring 38, as indicated at 53 in FIG. 5B, which pushes shaft 34 further down within central channel 32 until lateral aperture 44 on shaft 34 aligns with bottom aperture 58 which opens into internal compartment 24 (FIG. 5B). With the two apertures aligned (and the user still compressing dispenser cap 36), liquid medication 60 (FIG. 5B), which is stored in compartment 24, drips into hollow bottom portion 42 of shaft 34 and out of open dispenser tip 62 (FIG. 5B) under force of gravity, as indicated at directional arrow G in FIG. 5B, allowing the user to dispense liquid medication 60 in a controlled manner.

The user may control the rate of fluid (liquid medication) flow by manually varying the orientation of open dispenser tip 62 relative to a horizontal surface. A person skilled in the art would appreciate that the size and shape of the compartment and shaft apertures, as well as the type of material(s) used to manufacture the shaft and internal compartments, and the shape and volume capacity of the hollow bottom portion of the shaft and/or each internal compartment should be configured to minimize fluid (liquid medication) viscosity. For example, one oral antibiotic commonly sold by Pfizer, Inc. of Cambridge, Mass. under the trademark ZITHROMAX is known for its relatively high viscosity when the powder form of this medication is mixed with water at the pharmacy before the medication is sold in liquid form to parents/caregivers of young children.

FIG. 5B generally shows hollow bottom portion 42 of shaft 34 being full of liquid medication 60 which drips out of open dispenser tip 62. Hollow bottom portion 42 is appropriately apertured at 63 to allow for fluid flow, as indicated in reference to FIG. 7.

After all or part of a pre-set amount of liquid medication 60 has been dispensed from internal compartment 24, the user releases dispenser cap 36 which is then automatically pushed up, as indicated at 55 in FIG. 5A, to its rest position over top ring 38 by spring 40. At the next pre-set time interval for taking medication, the user may rotate dispenser cap 36 again until it aligns with another filled compartment and conveniently dispense the liquid medication in the manner generally described hereinabove in reference to FIG. 5B.

The liquid medication dispenser of the present invention makes medication management easier than ever. The housing and associated components may be manufactured from plastic or other suitable material(s) that are easy to maintain. The medication compartments provided internally within the housing may also be used to store pills in powder form, if needed. However, dispensing of medication in powder form may require appropriate modification of one or more components of the present invention, as needed.

The liquid medication dispenser of the present invention provides a convenient, secure and portable means to organize, store and administer liquid medicine to patients of relatively young age. The liquid medication dispenser of the present invention is simple to use and easy to carry around, as needed. For example, the dispenser may be carried around in a purse, baby accessory bag and/or the like. The dispenser may be marketed by pharmaceutical companies, pharmacies and/or other vendors with all four compartments pre-filled with liquid medication, i.e. as a convenient one-day supply for the young or adult patient. A person skilled in the art would readily appreciate that the spring-action cap utilized by the liquid medication dispenser of the present invention may be conveniently handled by the user with one hand only.

The exemplary embodiments described hereinabove are merely illustrative of the general principles of the present invention. Various design modifications may be employed that would reside within the scope of the invention. For example the housing of the present invention may be modified to contain more or less than four internal compartments, as needed. Thus, by way of example, but not of limitation, various alternative configurations may be utilized in accordance with the teachings herein. Accordingly, the drawings and description are illustrative and not meant to be a limitation thereof.

Moreover, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Thus, it is intended that the invention cover all embodiments and variations thereof as long as such embodiments and variations come within the scope of the appended claims and their equivalents.

What is claimed:

1. A liquid medication dispenser, comprising:

a housing with an open top, said housing including a central channel and a plurality of at internal compartments disposed around said central channel; a plurality of at least one bottom apertures on said central channel, wherein at least one opening is formed through said central channel into each of the plurality of internal compartments; and a rotatable shaft within said central channel, said rotatable shaft including an elongated bottom hollow portion with a lateral aperture thereon, said rotatable shaft in a first position preventing a liquid in any of said plurality of internal compartments from being transferred into said rotatable shaft, said rotatable shaft depressed into a second position moving said rotatable shaft downward to allow the elongated bottom portion to be in fluid communication with a desired one of said plurality of internal compartments, said elongated bottom hollow portion in fluid communication with a desired one of said plurality of internal compartments when said lateral shaft aperture is aligned with a desired one of said plurality of bottom channel apertures, said lateral aperture aligned at a pre-set distance and rotated a pre-set amount within said central channel, said fluid communication transferring liquid medication under gravity from a desired one of said plurality of internal compartments into said elongated bottom hollow portion, said elongated bottom hollow portion being apertured at one end to allow transferred liquid medication to drip out in a controlled fashion, wherein said rotatable shaft returns to said first position preventing said liquid in any of said plurality of internal compartments from being transferred into said rotatable shaft when said rotatable shaft is no longer depressed.

2. The liquid medication dispenser of claim 1, further comprising a cap.

3. The liquid medication dispenser of claim 2, further comprising a top ring fixed over the open top of said housing, said top ring including a central opening.

4. The liquid medication dispenser of claim 3, further comprising at least one spring which is operatively coupled between said top ring and said cap.

5. The liquid medication dispenser of claim 4, wherein said shaft further includes a solid ribbed top portion which is frictionally fitted through said central opening of said top ring and secured to the underside of said dispenser cap via said at least one spring.

6. The liquid medication dispenser of claim 5, wherein said shaft further includes a ribbed intermediate portion which is coupled between said top and bottom portions of said shaft.

7. The liquid medication dispenser of claim 6, wherein said at least one spring is biased away from said top ring.

8. The liquid medication dispenser of claim 3, wherein said top ring is over the open top of said housing.

9. The liquid medication dispenser of claim 8, wherein said top ring includes at least one side tab.

10. The liquid medication dispenser of claim 7, wherein said cap is rotatable with said rotatable shaft within said central channel.

11. The liquid medication dispenser of claim 10, wherein said at least one spring is rotatable with said dispenser cap relative to said top ring, said top ring fixed over said housing.

12. The liquid medication dispenser of claim 11, wherein the top surface of said dispenser cap is etched with at least one arrow-shaped marking.

13. The liquid medication dispenser of claim 12, wherein an outer wall of said housing is provided with at least one marking signifying selection of a respective internal compartment.

14. The liquid medication dispenser of claim 13, wherein said dispenser cap is rotated until said at least one arrow-shaped marking aligns with said at least one housing marking.

15. The liquid medication dispenser of claim 14, wherein said dispenser cap compresses toward said top ring when said at least one arrow-shaped marking is aligned with said at least one housing marking.

16. The liquid medication dispenser of claim 15, wherein said cap compression results in said shaft being advanced further within said central channel until said lateral shaft aperture aligns with said at least one bottom channel aperture.

17. The liquid medication dispenser of claim 16, wherein said housing is provided with an open dispenser tip.

18. The liquid medication dispenser of claim 17, wherein the rate of liquid medication drip out of said open dispenser tip is controlled by varying the orientation of said open dispenser tip relative to a horizontal surface.

19. The liquid medication dispenser of claim 1, wherein each of said lateral shaft aperture and said at least one bottom channel aperture minimizes viscosity.

20. A liquid medication dispenser, comprising:

a housing with an open top, said housing including a central channel and two or more internal compartments disposed around said central channel;

a top ring fixed over the open top of said housing, said top ring having a central opening; a dispenser cap disposed over said top ring; at least one spring operatively coupled between said dispenser cap and said top ring, said at least one spring being naturally biased away from said top ring; a plurality of bottom apertures on said central channel, wherein at least one bottom aperture on said central channel is in communication with each internal compartment; and a rotatable shaft secured at one end to the underside of said dispenser cap via said central opening of said top ring and said at least one spring, said rotatable shaft within said central channel, said rotatable shaft including an elongated bottom hollow portion with a lateral aperture thereon, said rotatable shaft in a first position preventing a liquid in any of said two or more internal compartments from being transferred into said rotatable shaft, said rotatable shaft depressed into a second position moving said rotatable shaft downward to allow the elongated bottom portion to be in fluid communication with a desired one of said two or more internal compartments, said elongated bottom hollow portion in fluid communication with an internal compartment of said two or more internal compartments when said lateral shaft aperture is aligned with said at least one bottom aperture, said rotatable shaft is aligned at a pre-set distance and rotated a pre-set amount within said central channel, said fluid communication transferring liquid medication under gravity from said internal compartment into said elongated bottom hollow portion, said elongated bottom hollow portion being apertured at one end to allow transferred liquid medication to drip out in a controlled fashion, wherein said rotatable shaft returns to said first position preventing said liquid in any of said two or more internal compartments from being transferred into said rotatable shaft when said rotatable shaft is no longer depressed.

21. The liquid medication dispenser of claim 20, wherein said top ring includes at least one side tab.

22. The liquid medication dispenser of claim 21, wherein said dispenser cap is rotatable with said rotatable shaft within said central channel.

23. The liquid medication dispenser of claim 22, wherein said at least one spring is rotatable with said dispenser cap relative to said top ring, said top ring fixed over said housing.

24. The liquid medication dispenser of claim 23, wherein the top surface of said dispenser cap is etched with a primary marking.

25. The liquid medication dispenser of claim 24, wherein the outer wall of said housing is provided with a plurality of secondary markings with each one signifying selection of a respective internal compartment.

26. The liquid medication dispenser of claim 25, wherein said dispenser cap is rotated until said primary marking aligns with one of said secondary markings.

27. The liquid medication dispenser of claim 26, wherein said dispenser cap compresses toward said top ring when said primary marking is aligned with one of said secondary markings.

28. The liquid medication dispenser of claim 27, wherein said cap compression results in said shaft being advanced further within said central channel until said lateral shaft aperture aligns with said at least one bottom channel aperture.

29. The liquid medication dispenser of claim 28, wherein said housing is provided with an open dispenser tip.

30. The liquid medication dispenser of claim 29, wherein the rate of liquid medication drip out of said open dispenser tip is controlled by varying the orientation of said open dispenser tip relative to a horizontal surface.

31. The liquid medication dispenser of claim 30, wherein each of said lateral shaft aperture and said at least one bottom channel aperture is configured to minimize viscosity.

32. A liquid medication dispenser, comprising:

a housing including: an open top; an open dispenser tip disposed away from said open top; a central channel connecting said open top and said open dispenser tip;

four internal compartments disposed around said central channel; and an outer wall provided with a plurality of markings, each of said markings signifying selection of a respective internal compartment; a top ring fixed over said open top of said housing, said top ring having a central opening a dispenser cap disposed over said top ring, wherein the top surface of said dispenser cap is marked in at least one location; at least one spring operatively coupled between said dispenser cap and said top ring, said at least one spring being naturally biased away from said top ring; a plurality of bottom apertures on said central channel wherein at least one bottom aperture on said central channel is in communication with each internal compartment; and a rotatable shaft secured at one end to the underside of said dispenser cap via said central opening of said top ring and said at least one spring, said rotatable shaft within said central channel, said rotatable shaft including an elongated bottom hollow portion with a lateral aperture thereon, said rotatable shaft in a first position preventing a liquid in any of said four internal compartments from being transferred into said rotatable shaft, said rotatable shaft depressed into a second position moving said rotatable shaft downward to allow the elongated bottom portion to be in fluid communication with a desired one of said four internal compartments said elongated bottom hollow portion in fluid communication with an internal compartment of said four compartments when said lateral shaft aperture is aligned with said at least one bottom aperture for said internal compartment, said rotatable shaft is aligned at a pre-set distance and rotated a pre-set amount within said central channel, said fluid communication transferring liquid medication under gravity from said internal compartment into said elongated bottom hollow portion, said elongated bottom hollow portion being apertured over said open dispenser tip to allow transferred liquid medication to drip out of said open dispenser tip in a controlled fashion, wherein the rate of liquid medication drip out of said open dispenser tip is controlled by varying the orientation of said dispenser tip relative to a horizontal surface, wherein said rotatable shaft returns to said first position preventing said liquid in any of said four internal compartments from being transferred into said rotatable shaft when said rotatable shaft is no longer depressed.

33. The liquid medication dispenser of claim 32, wherein said lateral shaft aperture minimizes viscosity.

34. The liquid medication dispenser of claim 32, wherein said at least one bottom channel aperture minimizes viscosity.

35. The liquid medication dispenser of claim 32, wherein said top ring includes at least one side tab.

* * * * *